United States Patent
Kubota

(10) Patent No.: US 10,478,060 B2
(45) Date of Patent: Nov. 19, 2019

(54) OPHTHALMIC IMAGE PROCESSING APPARATUS AND OPHTHALMIC IMAGING APPARATUS

(71) Applicant: TOPCON CORPORATION, Itabashi-ku, Tokyo (JP)

(72) Inventor: Atsushi Kubota, Itabashi-ku (JP)

(73) Assignee: TOPCON CORPORATION, Itabashi-ku, Tokyo (JP)

(*) Notice: Subject to any disclaimer, the term of this patent is extended or adjusted under 35 U.S.C. 154(b) by 73 days.

(21) Appl. No.: 15/649,826

(22) Filed: Jul. 14, 2017

(65) Prior Publication Data
US 2018/0028056 A1 Feb. 1, 2018

(30) Foreign Application Priority Data

Jul. 27, 2016 (JP) .................. 2016-147117

(51) Int. Cl.
| A61B 3/00 | (2006.01) |
| A61B 3/10 | (2006.01) |
| G06T 7/12 | (2017.01) |
| G06T 5/00 | (2006.01) |
| A61B 3/12 | (2006.01) |

(52) U.S. Cl.
CPC ............ *A61B 3/102* (2013.01); *A61B 3/0025* (2013.01); *A61B 3/0058* (2013.01); *G06T 5/008* (2013.01); *G06T 7/12* (2017.01); *A61B 3/1233* (2013.01); *G06T 2200/04* (2013.01); *G06T 2207/10101* (2013.01); *G06T 2207/30041* (2013.01)

(58) Field of Classification Search
CPC ..... A61B 3/0058; A61B 3/0075; A61B 3/101; A61B 3/1233; A61B 3/1241; A61B 3/0008; A61B 3/0025; A61B 3/0041; A61B 3/102; G06T 7/10; G06T 7/11; G06T 7/12; G06T 7/174; G06T 2207/30041
See application file for complete search history.

(56) References Cited

U.S. PATENT DOCUMENTS

| 2011/0116694 A1* | 5/2011 | Gareau .............. G01N 21/6458 382/128 |
| 2011/0141259 A1* | 6/2011 | Nakano ................ A61B 3/0025 348/78 |
| 2013/0301008 A1 | 11/2013 | Srivastava et al. |

(Continued)

FOREIGN PATENT DOCUMENTS

JP 2015-515894 A 6/2015

*Primary Examiner* — Jordan M Schwartz
(74) *Attorney, Agent, or Firm* — Chiesa Shahinian & Giantomasi PC

(57) ABSTRACT

An ophthalmic image processing apparatus of an embodiment includes a storage unit, a first brightness profile generation unit, a second brightness profile generation unit, and a brightness correction unit. The storage unit is configured to store image data acquired through scanning a subject's eye using optical coherence tomography. The first brightness profile generation unit is configured to generate a first brightness profile along a first direction by integrating brightness values of the image data. The second brightness profile generation unit is configured to process the first brightness profile to generate a second brightness profile. The brightness correction unit is configured to perform brightness correction of the image data based on the first brightness profile and the second brightness profile.

10 Claims, 10 Drawing Sheets

(56) References Cited

U.S. PATENT DOCUMENTS

| | | | |
|---|---|---|---|
| 2014/0055745 A1* | 2/2014 | Sato | A61B 3/102 |
| | | | 351/206 |
| 2014/0197835 A1* | 7/2014 | Kamada | G01R 33/4824 |
| | | | 324/309 |
| 2016/0213512 A1* | 7/2016 | Palanker | A61F 9/00736 |
| 2016/0317029 A1 | 11/2016 | Srivastava et al. | |
| 2017/0032547 A1* | 2/2017 | Dennerlein | G06T 5/002 |

* cited by examiner

OPHTHALMIC IMAGE PROCESSING APPARATUS AND OPHTHALMIC IMAGING APPARATUS

CROSS-REFERENCE TO RELATED APPLICATION

This application is based upon and claims the benefit of priority from Japanese Patent Application No. 2016-147117, filed Jul. 27, 2016; the entire contents of which are incorporated herein by reference.

FIELD

Embodiments described herein relate generally to an ophthalmic image processing apparatus and an ophthalmic imaging apparatus.

BACKGROUND

Diagnostic imaging occupies an important position in the field of ophthalmology. In recent years, utilization of optical coherence tomography (OCT) has advanced. OCT is being used not only for acquiring B mode images and three-dimensional images of a subject's eye but also for acquiring front images such as C mode images and shadowgrams. In addition, acquiring an image that emphasizes a specific site of the subject's eye, and acquiring functional information are also performed.

For example, OCT angiography, which forms an image in which retinal blood vessels and choroidal blood vessels are emphasized, is attracting attention (for example, refer to Japanese Translation of PCT International Application Publication No. 2015-515894). In OCT angiography, the same site of the fundus (e.g., the same cross sections) is scanned multiple times. In general, the tissue (i.e. structure) of the scanned site is invariant in time, but the blood flow portion inside the blood vessel changes with time. In OCT angiography, an image is formed by emphasizing a portion where such temporal change exists (i.e., emphasizing blood flow signals). By performing such iterative scanning and signal processing on a plurality of cross sections, a three-dimensional distribution of fundus blood vessels is obtained.

However, in OCT angiography, if fixation displacement occurs during multiple scans of the same site of the fundus of the subject's eye, the portion where the deviation occurs is emphasized as a portion where the above temporal change exists, and hence the portion is depicted as an artifact extending linearly in the scanning direction. It is difficult to completely remove this type of noise even with tracking that moves the OCT optical system or controls the scanning position according to the movement of the subject's eye.

In addition, in the image obtained in the manner as described above, the blood vessel regions and the artifact regions are emphasized. Therefore, the artifact regions are also included in the analysis target in the image, which lowers the reliability of the analysis result.

BRIEF SUMMARY

An ophthalmic image processing apparatus of an embodiment includes a storage unit, a first brightness profile generation unit, a second brightness profile generation unit, and a brightness correction unit. The storage unit is configured to store image data acquired through scanning a subject's eye using optical coherence tomography. The first brightness profile generation unit is configured to generate a first brightness profile along a first direction by integrating brightness values of the image data. The second brightness profile generation unit is configured to process the first brightness profile to generate a second brightness profile. The brightness correction unit is configured to perform brightness correction of the image data based on the first brightness profile and the second brightness profile.

DETAILED DESCRIPTION

Figure 1:
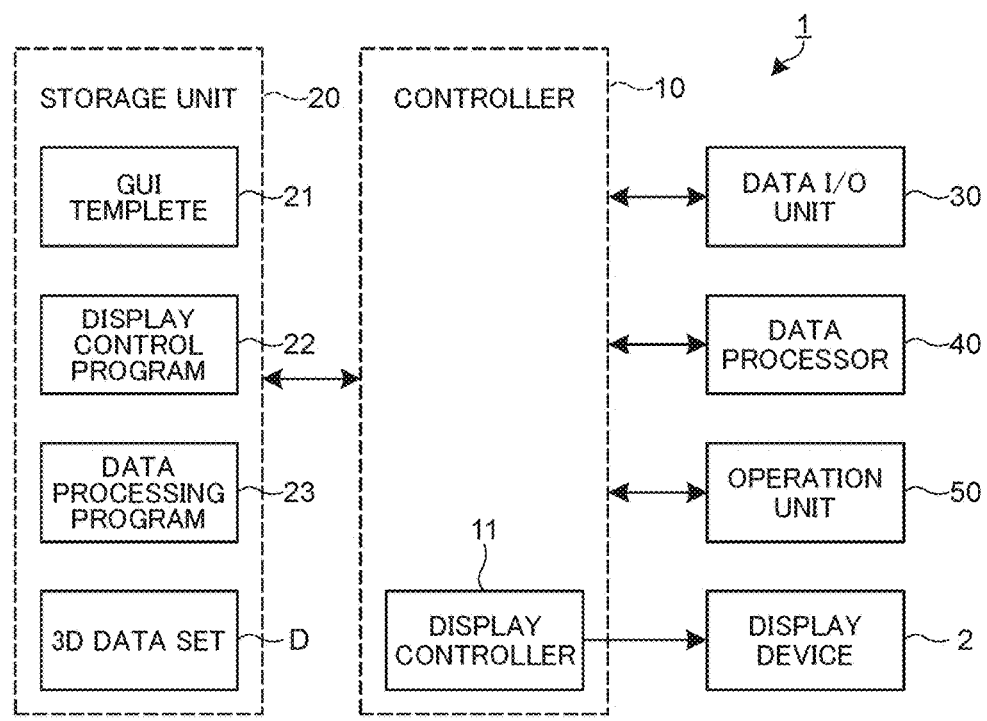
FIG. 1 is a schematic diagram illustrating an example of the configuration of the ophthalmic image processing apparatus according to the embodiment.

Exemplary embodiments of an ophthalmic image processing apparatus and an ophthalmic imaging apparatus according to the present invention will be described in detail with reference to the drawings. Any of the contents of the documents cited in the present specification and arbitrary known techniques may be applied to the embodiments below.

The embodiment provides a graphical user interface (GUI) for observing the images of a subject's eye. The GUI is used to observe at least OCT images. Types of the OCT images include an image in an arbitrary cross section mode, a shadowgram obtained by projecting an arbitrary area of three-dimensional data set, a blood vessel enhanced image (i.e., angiogram), and the like. Types of the image in an arbitrary cross section mode include a B mode image, a C mode image, a multi planar reconstruction (MPR) image, and the like. Types of the three-dimensional data set include volume data (voxel data), stack data, and the like. A blood vessel enhanced image is formed based on a three-dimensional data set composed from a plurality of two-dimensional data sets obtained through iteratively scanning substantially the same area of the subject's eye, for example. The three-dimensional data set is acquired through the following steps, for example: each of a plurality of B cross sections BX1, BX2, . . . , BXn is scanned a predetermined number of times (for example, 4 times); a predetermined number of B mode images (for example, 4 B mode images) are formed for each B cross section BXi (i=1, 2, . . . n); and the B mode images thus obtained are embedded in the same three-dimensional coordinate system (and are further voxelized). Such an image forming technique is known. In some cases in the following description, the horizontal direction (i.e., left/right direction) of the fundus of the subject's eye is regarded as the X direction, the vertical direction (i.e., up/down direction) is regarded as the Y direction, and the optical axis direction (i.e., depth direction) of the optical system for performing the OCT is regarded as the Z direction. Further, in some cases in the following description, an image and image data representing the concerned image may be regarded in the same manner.

The ophthalmic image processing apparatus of the embodiment has a function of forming an image from a three-dimensional data set (a rendering function, an image forming unit). The ophthalmic image processing apparatus acquires a three-dimensional data set acquired by an ophthalmic OCT apparatus via a network (in-house LAN, etc.) or a recording medium and renders the three-dimensional data set according to an instruction from a user or a computer, thereby forming an image for observation. Note that the ophthalmic image processing apparatus may include a display device on which an image is displayed.

In addition to the ophthalmic image processing apparatus as described above, the ophthalmic imaging apparatus of the embodiment includes an optical system, a drive system, a control system, and a data processing system for performing OCT. The ophthalmic imaging apparatus is configured to be capable of performing, for example, Fourier domain OCT (in other words, frequency domain OCT). The Fourier domain OCT includes spectral domain OCT and swept source OCT. The spectral domain OCT is a technique of imaging the subject's eye by acquiring the spectra of interference light in a space-divisional manner using a broadband low coherence light source and a spectroscope and subjecting it to Fourier transform. The swept source OCT is a technique of imaging the subject's eye by acquiring the spectra of interference light by time-divisional manner using a wavelength sweep light source (wavelength tunable light source) and a photodetector (e.g., balanced photodiode etc.) and subjecting it to Fourier transform. The ophthalmic imaging apparatus may include a modality other than OCT. Such a modality may be a fundus camera, a scanning laser ophthalmoscope (SLO), a slit lamp microscope, an ophthalmic surgical microscope, or the like.

<Ophthalmic Image Processing Apparatus>

[Configuration Examples]

Figure 2:
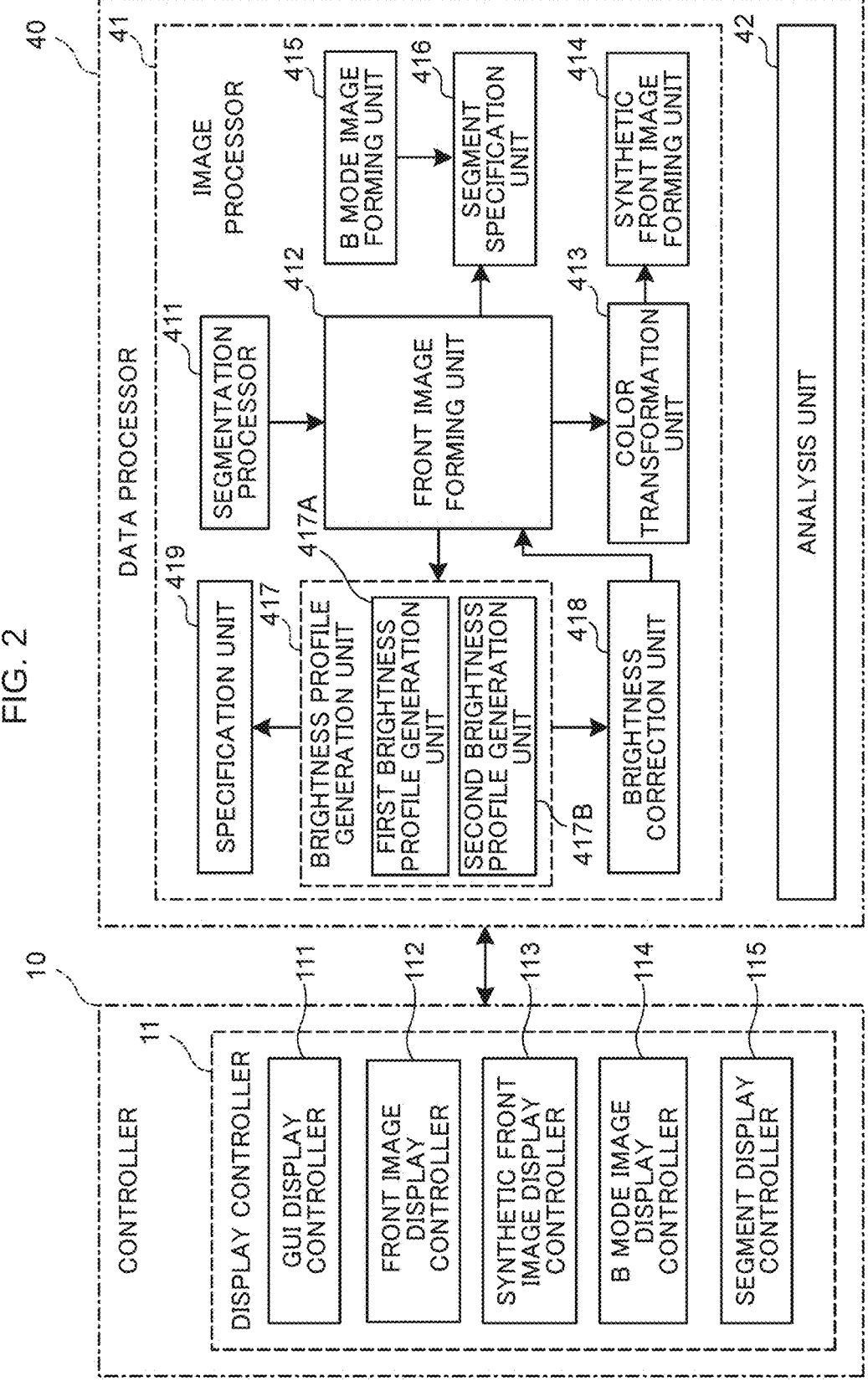
FIG. 2 is a schematic diagram illustrating an example of the configuration of the ophthalmic image processing apparatus according to the embodiment.

An embodiment of an ophthalmic image processing apparatus will be described. FIG. 1 and FIG. 2 show an exemplary configuration of the ophthalmic image processing apparatus according to the embodiment. The ophthalmic image processing apparatus 1 controls the display device 2 to display a GUI for observing images of the subject's eye and various information related to the subject's eye. The display device 2 may be a part of the ophthalmic image processing apparatus 1 or may be an external device connected to the ophthalmic image processing apparatus 1.

The ophthalmic image processing apparatus 1 includes the controller 10, the storage unit 20, the data input and output unit (data I/O unit) 30, the data processor 40, and the operation unit 50.

(Controller 10)

The controller 10 controls each part of the ophthalmic image processing apparatus 1. The controller 10 includes a processor. In this specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The controller 10 realizes the functions according to the embodiment, for example, by reading out and executing a program stored in a storage circuit or a storage device (storage unit 20 or the like).

The controller 10 includes the display controller 11. The display controller 11 performs control for the display device 2 to display information. The display controller 11 can perform the display control based on information stored in the storage unit 20.

As shown in FIG. 2, the display controller 11 includes the GUI display controller 111, the front image display controller 112, the synthetic front image display controller 113, the B mode image display controller 114, and the segment display controller 115.

Based on the GUI template 21 and the display control program 22 stored in the storage unit 20, the GUI display controller 111 controls the display device 2 to display screens, dialogs, icons, and the like as GUIs.

Based on the display control program 22, the front image display controller 112 displays a front image such as a C mode image, a shadowgram, a blood vessel enhanced image (angiogram), and the like on the GUI screen. In the present embodiment, each of a plurality of front images formed from the three-dimensional data set D is displayed in a predetermined display region of the GUI screen.

The synthetic front image display controller 113 displays a synthetic image (a synthetic front image) of a plurality of front images of the subject's eye in a predetermined display region of the GUI screen. The synthetic front image may be an image formed based on a single image data or an image formed based on a plurality of image data. In the former case, the synthetic front image display controller 113 displays a synthetic front image formed by the data processor 40 on the GUI screen. In the latter case, the synthetic front image display controller 113 displays a plurality of images based on a plurality of image data one over another. Such display control is executed, for example, by using the layer display function. Specifically, the synthetic front image display controller 113 can perform processing of respectively displaying a plurality of images based on a plurality of image data in a plurality of layers, processing of setting the opacity (i.e., a value) of each layer, and processing of displaying these layers one over another.

The B mode image display controller 114 displays a B mode image formed from the three-dimensional data set D in a predetermined display region of the GUI screen.

The segment display controller 115 displays information that indicates the partial region of the B mode image corresponding to the slice area (i.e., segment) of the three-dimensional data set D represented by each front image on the GUI screen. Such information will be referred to as segment information. The segment information is displayed in the color assigned to the corresponding front image.

A specific example of processing performed by the display controller 11 (the GUI display controller 111, the front image display controller 112, the synthetic front image display controller 113, the B mode image display controller 114, and the segment display controller 115) will be described later.

(Storage Unit 20)

The storage unit 20 stores various kinds of information. In the present embodiment, the storage unit 20 stores the GUI template 21, the display control program 22, the data processing program 23, and the three-dimensional data set D. The three-dimensional data set D may be stack data or voxel data. The stack data is image data in which a plurality of B mode images is arranged in the Y direction (first direction), wherein each of the plurality of B mode images lies along the X direction (second direction) orthogonal to the Y direction. The voxel data is formed by applying interpolation to the stack data. The three-dimensional data set D is acquired using an ophthalmic OCT apparatus.

The storage unit 20 may store a two-dimensional data set. The two-dimensional data set may be image data of a two-dimensional image formed based on the three-dimensional data set D or image data of a two-dimensional image acquired by an ophthalmic OCT apparatus. The two-dimensional image may be a B mode image, a front image, an MPR image, or the like. The front image may be a projection image, an en-face image, an OCT angiography image (angiogram), a shadowgram image, or the like. The image data of the two-dimensional front image may be image data acquired through raster scan. For the raster scan, the ophthalmic OCT apparatus iterates one-dimensional scan in the Y direction (i.e., slow axis direction, vertical direction), wherein the one-dimensional scan is a scan of the fundus of the subject's eye in the X direction (i.e., fast axis direction, horizontal direction).

The GUI template 21 includes templates of screens, dialogs, icons, and the like displayed as GUIs on the display device 2.

The display control program 22 includes a program executed for the controller 10 to perform control of the GUI displayed based on the GUI template 21. In the present embodiment, the display control program 22 includes a program for the display controller 11 to perform control for displaying GUIs and images. The display control of the present embodiment is realized by cooperation of the display controller 11 as hardware (i.e., as a processor) and the display control program 22 as software. A specific example of the display processing will be described later.

The data processing program 23 includes a program executed for the data processor 40 (and the controller 10) to perform various kinds of data processing. The data processing of the present embodiment is realized by cooperation of the data processor 40 (and the controller 10) as hardware (i.e., as a processor) and the data processing program 23 as software. A specific example of the data processing will be described later.

The three-dimensional data set D will be described. The three-dimensional data set D is image data representing the state (e.g., morphology (e.g., structure, form, shape, etc.) a function, etc.) of the three-dimensional region of the subject's eye. The three-dimensional data set D may include image data in which positions of pixels (e.g., pixels, voxels, etc.) are defined by a three-dimensional coordinate system. Examples of such image data include stack data formed by embedding two or more pieces of B mode image data in a three-dimensional coordinate system, and volume data formed by converting pixels of stack data into voxels. Another example of the three-dimensional data set D may include a group of B mode image data whose pixel positions are defined by a two-dimensional coordinate system. As still another example, the three-dimensional data set D may be time-series image data or may be image data constructed from time-series image data. Examples of such image data include three-dimensional image data in which blood vessels are emphasized (i.e., a three-dimensional angiogram), image data representing blood flow dynamics in a plurality of vertical cross sections (B scan planes) or in three-dimensional regions, and the like. The type of the three-dimensional data set D is arbitrary, and the three-dimensional data set D is formed using a known OCT technique corresponding to the type.

The three-dimensional data set D formed by the ophthalmic OCT apparatus (or by the computer that processes the data acquired by the OCT apparatus) is transmitted to and stored in an image management server installed in a medical institution, a network, or the like, for example. Supplementary information is associated with the three-dimensional data set D. The supplementary information includes subject identification information (e.g., patient ID, etc.), identification information of left eye/right eye, imaging date and time, medical institution identification information, and the like. As a specific operation example, three-dimensional data set D is managed in the digital imaging and communication in medicine (DICOM) format, and at least part of the supplementary information is included in DICOM tag information. Alternatively, three-dimensional data set D may be managed in association with the electronic medical record of the subject. In response to receiving a request from the ophthalmic image processing apparatus 1, the image management server retrieves the three-dimensional data set D of the concerned subject and sends it to the ophthalmic image processing apparatus 1. As another operation example, when three-dimensional data set D is stored in a portable recording medium, a mobile computer, or the like, three-dimensional data set D may be read out from the portable recording medium or the like using a reader/writer (described later) of the ophthalmic image processing apparatus 1. The three-dimensional data set D thus inputted is stored in the storage unit 20 by the controller 10.

The site of the subject's eye represented by the three-dimensional data set D is arbitrary, and may include, for example, at least one of the followings: the fundus (the retina, the choroid, the sclera, etc.); the vitreous body; the crystalline lens; the anterior segment (the cornea, the anterior chamber, the iris, the crystalline lens, the ciliary body, the Zinn's zonule, etc.); and an eyelid. Hereinafter, a typical example of the three-dimensional data set D will be described wherein the three-dimensional data set D is obtained by applying OCT scan to the three-dimensional region of the subject's eye that includes part of the fundus and part of the vitreous body.

(Data Input and Output Unit 30)

The data input and output unit 30 performs input of data to the ophthalmic image processing apparatus 1 and output of data from the ophthalmic image processing apparatus 1. It should be noted that the data input and output unit 30 may be configured to only input or output data. The data input and output unit 30 may include, for example, a communication device for sending and receiving data via a communication line such as a LAN, the Internet, a dedicated line, etc. The data input and output unit 30 may include a reader/writer for reading data from a recording medium and writing data to a recording medium. Further, the data input and output unit 30 may include a scanner that reads information recorded on a print medium or the like, a printer that records information on a paper medium, or the like.

(Data Processor 40)

The data processor 40 includes a processor that executes the data processing program 23 and performs various data processing. For example, the data processor 40 applies image processing to image data of the subject's eye. As a typical example thereof, the data processor 40 performs rendering such as three-dimensional computer graphics (3DCG) or the like, processing of removing or reducing artifacts included in an image formed based on the three-dimensional data set D, processing analyzing an image formed based on the three-dimensional data set D, or the like.

As shown in FIG. 2, the data processor 40 includes the image processor 41 and the analysis unit 42.

(Image Processor 41)

The image processor 41 forms various kinds of images based on the three-dimensional data set D. For example, based on the three-dimensional data set D, the image processor 41 forms a B mode image, a plurality of front images, and a synthetic front image. The synthetic front image is constructed by synthesizing (at least part of) the plurality of front images. The image data of the image generated by the image processor 41 is stored in the storage unit 20. In such processes, the image processor 41 can execute removal or reduction of the artifacts depicted in the image formed based on the three-dimensional data set D.

The image processor 41 includes the segmentation processor 411, the front image forming unit 412, the color transformation unit 413, the synthetic front image forming unit 414, the B mode image forming unit 415, the segment specification unit 416, the brightness profile generation unit 417, the brightness correction unit 418, and the specification unit 419.

The segmentation processor 411 analyzes the three-dimensional data set D to specify a plurality of partial data sets corresponding to a plurality of tissues of the subject's eye. Segmentation is image processing for determining specific tissues and/or tissue boundaries, and is widely used in the ophthalmic OCT field. For example, the segmentation processor 411 determines the gradients of the pixel values (i.e., brightness values) in each A mode image included in the three-dimensional data set D, and specifies a position where the gradient value is large to be a tissue boundary. Note that the A mode image is one-dimensional image data extending in the depth direction of the fundus. The depth direction of the fundus is defined as, for example, the Z direction, the incident direction of the OCT measurement light, the axial direction, the optical axis direction of the objective lens, or the like.

In a typical example, the segmentation processor 411 specifies a plurality of partial data sets corresponding to a plurality of layer tissues of the fundus by analyzing the three-dimensional data set D representing the fundus (the retina, the choroid, etc.) and the vitreous body. Each partial data set is defined by the boundaries of a layer tissue. Examples of the layer tissue specified as a partial data set include sub-tissues of the retina such as the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer. As another example, it is possible to specify a partial data set corresponding to the Bruch membrane, the choroid, the sclera, the vitreous body, or the like. It is also possible to specify a partial data set corresponding to a lesion part. Examples of lesion parts include a detachment part, an edema, a bleeding site, a tumor, a drusen, and the like.

The front image forming unit 412 forms a plurality of front images based on at least part of the plurality of partial data sets specified by the segmentation processor 411. Each front image is an image showing a predetermined slice area of the three-dimensional data set D. The slice area, for example, has a thickness in the depth direction of the fundus. The slice area is set, for example, by the user or by the ophthalmic image processing apparatus 1.

The slice area may be a region corresponding to one or more of the plurality of partial data sets specified by the segmentation processor 411. For example, it is possible to take account of the slice area (surface layer portion) including the partial data set group corresponding to the area from the inner limiting membrane (ILM) to the inner plexiform layer (IPL), the slice area (retinal outer layer portion) including the partial data set group corresponding to the area from the outer nuclear layer (ONL) to the retinal pigment epithelium (RPE), the slice area including a partial data set group corresponding to the choroid (i.e., from the Bruch membrane (BM) to the choroid-sclera interface (CSI)), or the like. In this way, the thickness of the slice area (i.e., the distance between the boundaries in the Z direction) is not necessarily constant, but it is also possible to set a slice area of a constant thickness.

The front image forming unit 412 can form a front image by projecting the data included in the set slice area in the depth direction (i.e., Z directional projection). Such projection front image is referred to as a shadowgram. The projection front image that spans the entire area in the Z direction of the three-dimensional data set D is referred to as a projection image, and is used for the registration between a fundus photograph and the three-dimensional data set D, or the like. In addition, the front image forming unit 412 can also set a C mode image (i.e., en-face image) representing a transverse cross section (or, a XY cross section, a horizontal cross section) of the three-dimensional data set D as the front image. Further, the front image may be an arbitrary MPR image. For example, the MPR image may be an image of a cross section having a small oblique angle with respect to the XY plane).

The front image formed by the front image forming unit 412 may be an arbitrary type of OCT image, for example, may be an image representing the morphology of the subject's eye (i.e., ordinary OCT image), a blood vessel enhanced image (i.e., angiogram), or a blood flow dynamic image (i.e., phase image). In addition, the front image forming unit 412 can also form a front image by flattening the slice area corresponding to the layer (or layer boundary) specified by the segmentation processor 411 in parallel to the XY plane. Such an image is called a flattened image.

The color transformation unit 413 converts at least one of the plurality of front images formed by the front image forming unit 412 from a grayscale image to a color image. The color transformation unit 413 replaces values (brightness values) of at least part of the pixels of the front image with color values. The color values may be a constant value or values over a predetermined range. In addition, the color transformation unit 413 can perform processing of selecting pixels to be subjected to color conversion. This processing may include, for example, arbitrary kinds of image processing such as threshold processing on brightness value, shape analysis (pattern analysis, pattern matching, etc.), binarization, filter processing, or the like.

A specific example will be described. Let the front image be a blood vessel enhanced image (i.e., angiogram). Although not intended to be limiting, in a typical blood vessel enhanced image, pixels corresponding to blood vessels are expressed by relatively high brightness values. That is, pixels corresponding to blood vessels are expressed in white (bright) on a black background. The color transformation unit 413 extracts pixels (high brightness pixels) having relatively high brightness values from the pixels included in the front image by applying image processing such as threshold processing, binarization or high pass filtering, for example. Further, the color transformation unit 413 replaces the brightness value of each extracted pixel with a predetermined color value. The color represented by the color value is a color assigned in advance to the concerned front image. As will be described in detail later, the color assigned to the front image may be the same as (or similar to) the display color of the frame portion of the display region in the GUI screen on which the concerned front image is displayed. In addition, the same color value may be given to all the high brightness pixels, or different color values may be given according to the magnitude of the brightness value, for example. In the former case, a predetermined color value (default value) is given. As an example of the latter, there is color conversion using a color palette (i.e., look-up table) for a pseudo color display.

The synthetic front image forming unit 414 synthesizes a plurality of front images including at least part of one or more front images converted into color images by the color transformation unit 413. The image constructed in this way is called a synthetic front image. The registration between the plurality of front images is unnecessary since the plurality of front images to be synthesized are constructed from the same three-dimensional data set D. Alternatively, it is possible to apply natural registration to the plurality of front images based on the locations of the plurality of front images (i.e., the locations of the plurality of slice areas) in the three-dimensional data set D.

In the synthetic front image, objects (e.g., blood vessels, lesion parts, layer tissues, etc.) in the plurality of slice areas are expressed. Here, a mode of expressing the objects can be changed according to the positional relationship of the plurality of slice areas. For example, it is possible to preferentially present the objects in the slice area(s) on the side close to the fundus surface (i.e., inner limiting membrane). At least part of the objects expressed in the synthetic front image (e.g., blood vessels in a predetermined slice area with which color values are associated, etc.) are displayed in color.

As described above, when the synthetic front image display controller 113 displays the plurality of front images one over another by using the layer display function or the like, the synthetic front image forming unit 414 is unnecessary or its operation is stopped. In addition, the process related to the opacity (a values) of the layers is an alternative to the preferential presentation according to the slice areas (described above).

The B mode image forming unit 415 forms a B mode image representing a preset vertical cross section (the cross section orthogonal to the horizontal cross section) based on the three-dimensional data set D. Any known image processing such as MPR processing may be applied to the B mode image formation.

The segment specification unit 416 specifies the partial region of the B mode image formed by the B mode image forming unit 415 corresponding to the slice area (i.e., segment) of the three-dimensional data set D represented by the front image formed by the front image forming unit 412 (in particular, the front image used to form the synthetic front image). The specification of the partial region corresponds to the process of determining a common region between the target slice area and the vertical cross section of the B mode image.

The brightness profile generation unit 417 generates a distribution of brightness values in the Y direction of the image formed by the image processor 41. The distribution is referred to as a brightness profile. The brightness profile generation unit 417 includes the first brightness profile generation unit 417A and the second brightness profile generation unit 417B.

The first brightness profile generation unit 417A generates a first brightness profile along the Y direction by integrating the brightness values of the image data formed by the image processor 41. The Y direction is the slow axis direction orthogonal to the X direction which is the fast axis direction, and the first brightness profile is the slow axis brightness profile. For example, the first brightness profile generation unit 417A integrates the brightness values of the image formed by the image processor 41 in the X direction and divides the sum by the number of pixels in the X direction (i.e., averaging processing), thereby generating the brightness profile along the Y direction as the first brightness profile. The first brightness profile generation unit 417A may generate a first brightness profile in the same manner as described above from an image stored in the storage unit 20. The first brightness profile generation unit 417A may generate a brightness profile along the Y direction as the first brightness profile by integrating the brightness values in the X direction.

The second brightness profile generation unit 417B processes the first brightness profile generated by the first brightness profile generation unit 417A to generate a second brightness profile. For example, the second brightness profile generation unit 417B generates the second brightness profile by smoothing the first brightness profile. Here, the smoothing means processing to remove a jutting value, a value greatly apart from others, a singular value, or the like in the first brightness profile, or processing to bring such values close to other values, in order to achieve a state where there is no protrusion (or little protrusions) as a whole. In this way, the second brightness profile generation unit 417B can generate a second brightness profile by applying a smoothing filter to the first brightness profile. The smoothing filter may include at least one of a median filter, a rolling ball filter, a low pass filter, a high pass filter, and a moving average filter. In the present embodiment, the second brightness profile generation unit 417B applies at least one of the median filter and the rolling ball filter to the first brightness profile. The second brightness profile generation unit 417B may apply at least one of the median filter and the rolling ball filter to each of two or more partial brightness profiles obtained by dividing the first brightness profile into two or more regions in the X direction.

The second brightness profile generation unit 417B may process only part of the first brightness profile to generate the second brightness profile. With this, brightness correction performed by the brightness correction unit 418 described later can be performed locally.

Based on the first brightness profile and the second brightness profile, the brightness correction unit 418 applies brightness correction to the image data which is the source of the generation of the first brightness profile. More specifically, for each of a plurality of pixel positions in the Y direction, based on the value of the first brightness profile at the concerned pixel position in the Y direction and the value of the second brightness profile at the concerned pixel position in the Y direction, the brightness correction unit 418 performs brightness correction on the pixel of the image data corresponding to the concerned pixel position. At this time, the brightness correction unit 418 can perform the brightness correction based on the ratio or the difference between the value of the first brightness profile at the concerned pixel position in the Y direction and the value of the second brightness profile at the concerned pixel position in the Y direction.

In the present embodiment, the brightness correction unit 418 performs brightness correction based on the ratio or the difference between the value of the first brightness profile at each pixel position in the Y direction and the value of the second brightness profile at the corresponding pixel position in the Y direction according to the following formula (1).

$$C(x, y) = \frac{O(x, y)}{(Vp(y)/Fp(y))} \quad (1)$$

In the formula (1), x indicates a pixel position in the X direction (0≤x≤xW, where W is an integer equal to or larger than 1) and y indicates a pixel position in the Y direction (0≤xy≤xH, where H is an integer equal to or larger than 1). O (x, y) represents a brightness value at a pixel position (x, y) in the image that is the source of the generation of the first brightness profile. Vp (y) represents the first brightness profile, and Fp (y) represents the second brightness profile. As shown in the formula (1), the brightness correction unit 418 generates image data whose brightness values has been corrected by respectively dividing the brightness values of the original image by the ratios of the first brightness profile to the corresponding second brightness profile. The generated image data is stored in the storage unit 20. In this case, the image data on which the brightness correction has been performed by the brightness correction unit 418 is output as the image data of the front image formed by the front image forming unit 412. The image data on which the brightness correction has been performed may be output as image data of an image formed by the synthetic front image forming unit 414 or the B mode image forming unit 415. The display controller 11 can execute the display control described above based on the image data on which the brightness correction has been performed.

With reference to FIGS. 3, 4, 5A, and 5B, an operation example in the case of removing or reducing artifacts in an en-face image in which blood vessel regions are enhanced will be described.

Figure 3:
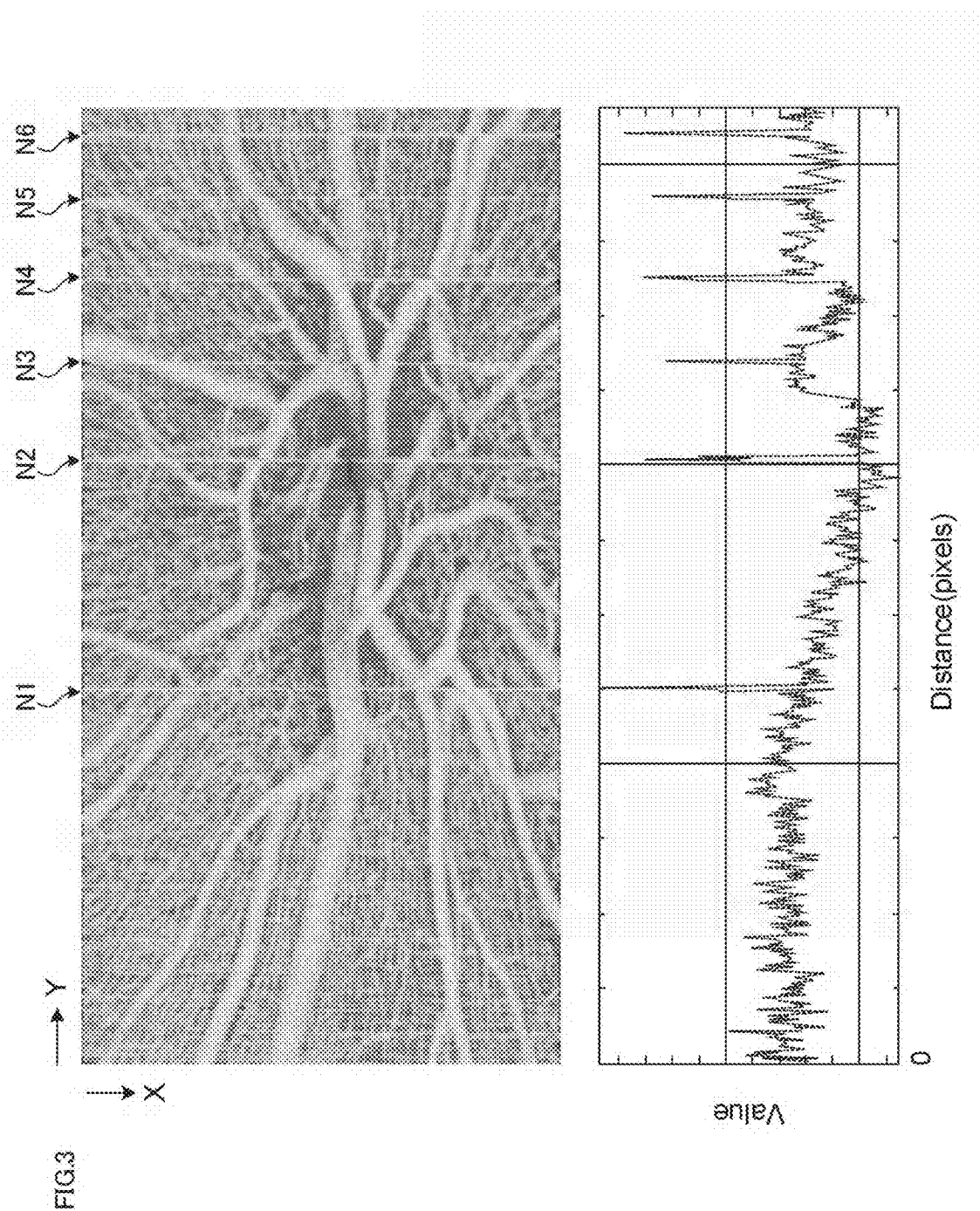
FIG. 3 is a diagram describing an example of the operation of the ophthalmic image processing apparatus according to the embodiment.

FIG. 3 is an explanatory diagram of the first brightness profile according to the present embodiment. FIG. 3 shows an explanatory diagram of the first brightness profile generated for the en-face image in which the horizontal direction corresponds to the X direction and the vertical direction corresponds to the Y direction. In this en-face image, there are artifacts N1 to N6 each extending in the X direction (i.e., fast axis direction) due to fixation displacement. In the first brightness profile generated by the first brightness profile generation unit 417A, since the brightness values are integrated in the X direction, the integrated values of the brightness values (or the average values of the brightness values) change in a spike-like shape at the positions corresponding to the lines where the artifacts N1 to N6 exist.

Figure 4:
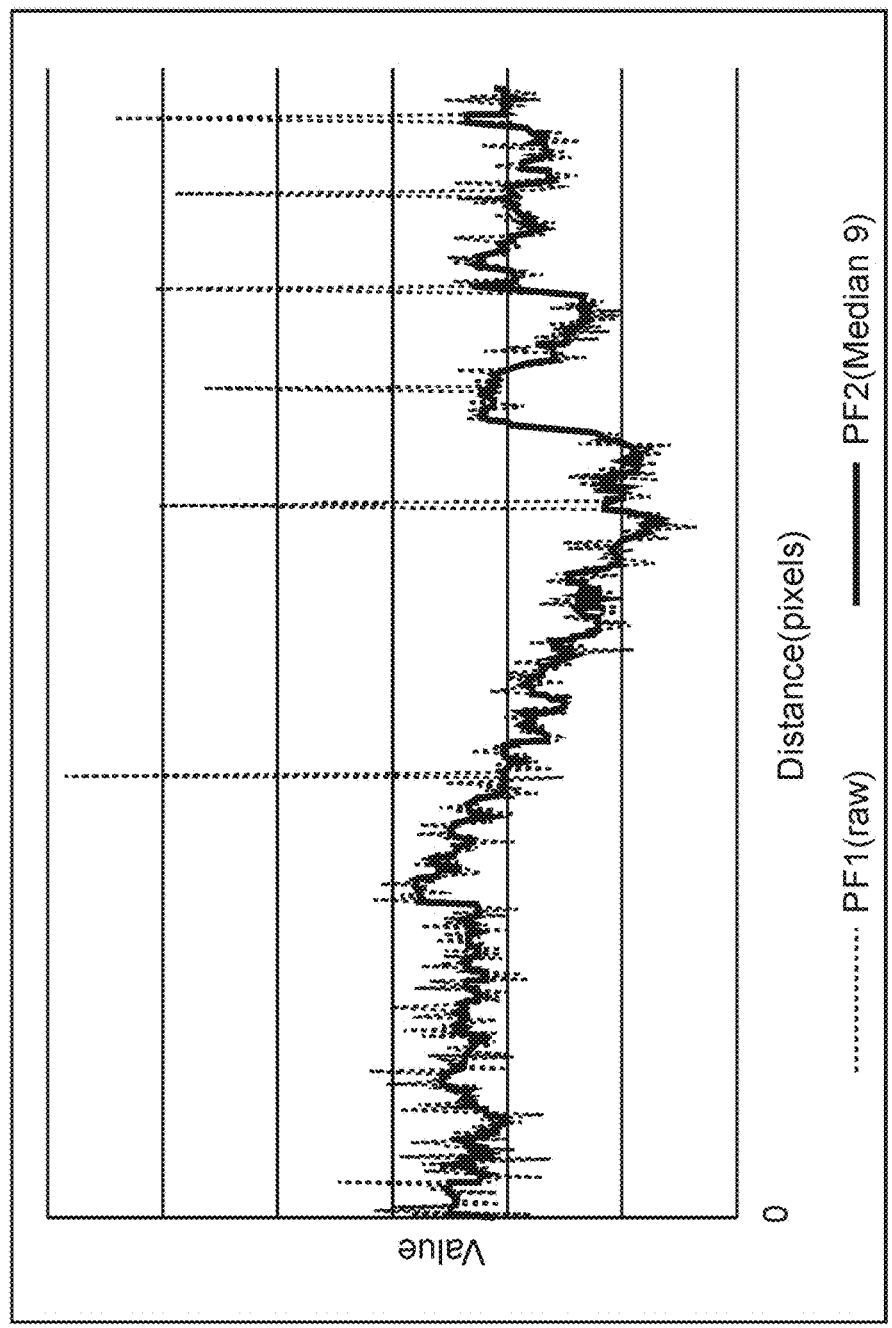
FIG. 4 is a diagram describing an example of the operation of the ophthalmic image processing apparatus according to the embodiment.

FIG. 4 is an explanatory diagram of the second brightness profile according to the present embodiment. The second brightness profile generation unit 417B generates the second brightness profile by applying a median filter having a median size of 9 to the first brightness profile, for example. As shown in FIG. 4, in the second brightness profile PF2, the portions that change in a spike-like shape in the first brightness profile PF1 are removed since the median value corresponding to the median size is determined.

Figure 5A:
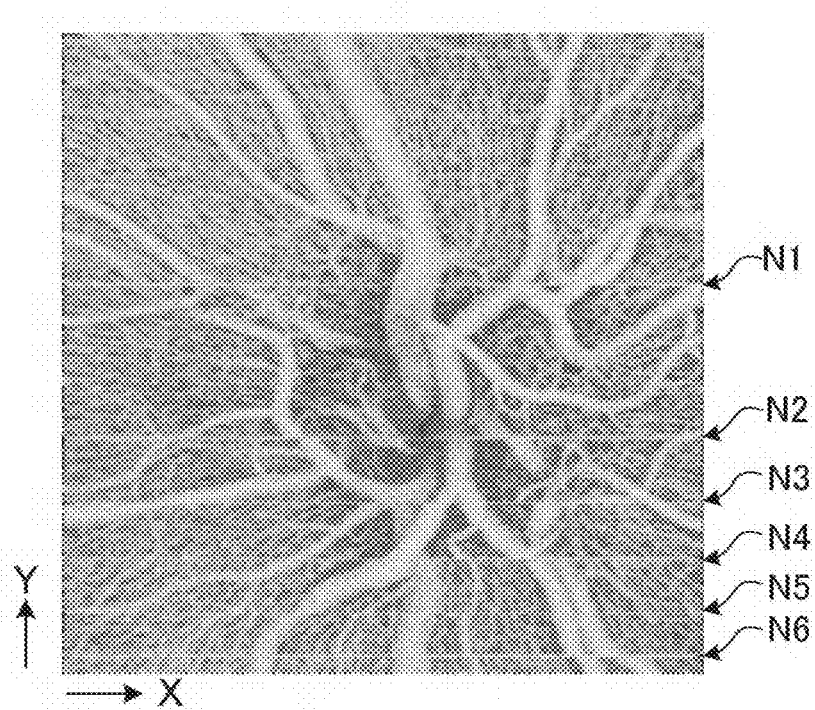
FIG. 5A is a diagram describing an example of the operation of the ophthalmic image processing apparatus according to the embodiment.
Figure 5B:
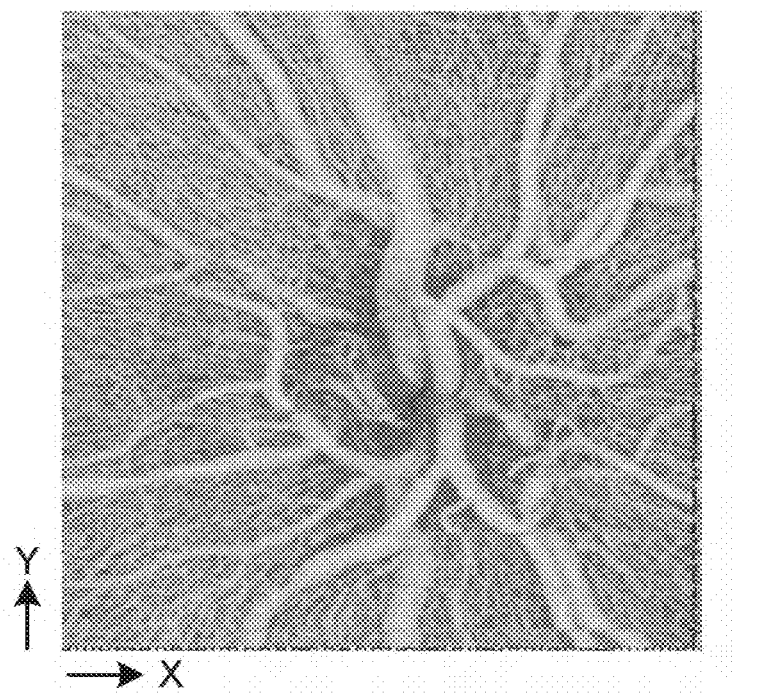
FIG. 5B is a diagram describing an example of the operation of the ophthalmic image processing apparatus according to the embodiment.

FIG. 5A and FIG. 5B show operation diagrams of the brightness correction unit 418. FIG. 5A shows an example of an original en-face image formed by the image processor 41 or an original en-face image stored in the storage unit 20. FIG. 5B shows an example of an en-face image obtained through the brightness correction performed by the brightness correction unit 418 on the original en-face image shown in FIG. 5A. In FIGS. 5A and 5B, the X direction and the Y direction are the same as those in FIG. 3. As shown in FIG. 5A, the artifacts N1 to N6 each extending in the X direction are depicted in this en-face image due to fixation displacement as in FIG. 3. The brightness correction unit 418 corrects the brightness values of the pixels of the original en-face image by dividing each original brightness value by the corresponding ratio of the first brightness profile to the second brightness profile as described above. As a result, as shown in FIG. 5B, an en-face image in which the artifacts N1 to N6 have been removed or reduced is obtained.

The specification unit 419 specifies a partial region of the image data based on the first brightness profile. For example, the specification unit 419 can specify an artifact region as the partial region of the image data. In this case, the specification unit 419 detects, as an artifact, a peak in the first brightness profile whose half width is equal to or less than a predetermined value and whose amplitude is equal to or larger than a predetermined level. The half width may be equal to or less than a predetermined value within a predetermined amplitude level. The predetermined amplitude level may be a fixed value, a relative value based on the first brightness profile, a value obtained by multiplying a value based on the standard deviation of the first brightness profile by a predetermined coefficient, or the like.

(Analysis Unit 42)

The analysis unit 42 executes a predetermined analysis process based on the image generated by the image processor 41. In the present embodiment, the analysis unit 42 can remove the artifact regions as the partial regions specified by the specification unit 419 from the image generated by the image processor 41, and execute the predetermined analysis process based on the resultant image.

For example, the analysis unit 42 removes the artifact regions specified by the specification unit 419 from the image generated by the image processor 41 and calculates the area (square measure) of an area with brightness levels equal to or higher than a predetermined level. More specifically, the analysis unit 42 removes the specified artifact regions from the blood vessel enhanced image generated by the image processor 41, and specifies an area with brightness levels equal to or higher than a predetermined level, thereby obtaining the area (square measure) of newborn blood vessels (NV) such as subfoveal choroidal neovascularization (CNV). With this, it becomes possible to carry out the follow-up of the effect of anti-vascular endothelial growth factor drug (Anti-VEGF drug) that inhibits the growth of NV without being affected by the artifacts.

For example, the analysis unit 42 removes the artifact regions specified by the specification unit 419 from the image generated by the image processor 41 and obtains the area (square measure) of an area with brightness level equal to or less than a predetermined level. More specifically, the analysis unit 42 removes the specified artifact regions from the blood vessel enhanced image generated by the image processor 41, and specifies an area with brightness level equal to or less than the predetermined level, thereby obtaining the area (square measure) of an ischemic region in diabetes (DM) or age-related macular degeneration (AMD). As a result, it becomes possible to carry out the follow-up of DM etc. without being affected by the artifacts.

For example, the analysis unit 42 removes the artifact region specified by the specification unit 419 from the image generated by the image processor 41, and determines the ratio corresponding to blood flows. More specifically, the analysis unit 42 obtains the ratio corresponding to blood flows by removing the specified artifact region from the blood vessel enhanced image (angiogram) generated by the image processor 41, and specifying the blood vessel regions. As a result, the ratio occupied by blood flows in capillary vessels can be more accurately determined. Therefore, it is possible to visualize the ischemic state due to DM, branch retinal vein occlusion (BRVO), Glaucoma, or the like, to visualize the distribution of capillary vessels in damaged sites, or to quantitatively carry out follow-ups, without being affected by the artifacts.

The functions of the data processor 40 are not limited to those mentioned above. For example, the data processor 40 may be capable of performing any of the functions that are described below or any known functions.

The segmentation processor 411 can perform segmentation processing on an image in which artifacts are removed or reduced by performing brightness correction by the brightness correction unit 418 as described above. With this, it becomes possible to more accurately specify a plurality of partial data sets corresponding to a plurality of layer tissues of the fundus, without being affected by the artifacts.

(Operation Unit 50)

The operation unit 50 is used by the user to input instructions to the ophthalmic image processing apparatus 1. The operation unit 50 may include a known operation device used for a computer. For example, the operation unit 50 may include a pointing device such as a mouse, a touch pad or a track ball. Further, the operation unit 50 may include a keyboard, a pen tablet, a dedicated operation panel, or the like. When the ophthalmic image processing apparatus 1 is connected to an ophthalmic apparatus (for example, an OCT apparatus), an instruction can be input to the ophthalmic image processing apparatus 1 by using an operation device (e.g., a joystick, a button, a switch, etc.) provided in the ophthalmic apparatus. In that case, the operation unit 50 includes such an operation device of the ophthalmic apparatus.

[Operation Examples]

Figure 6:
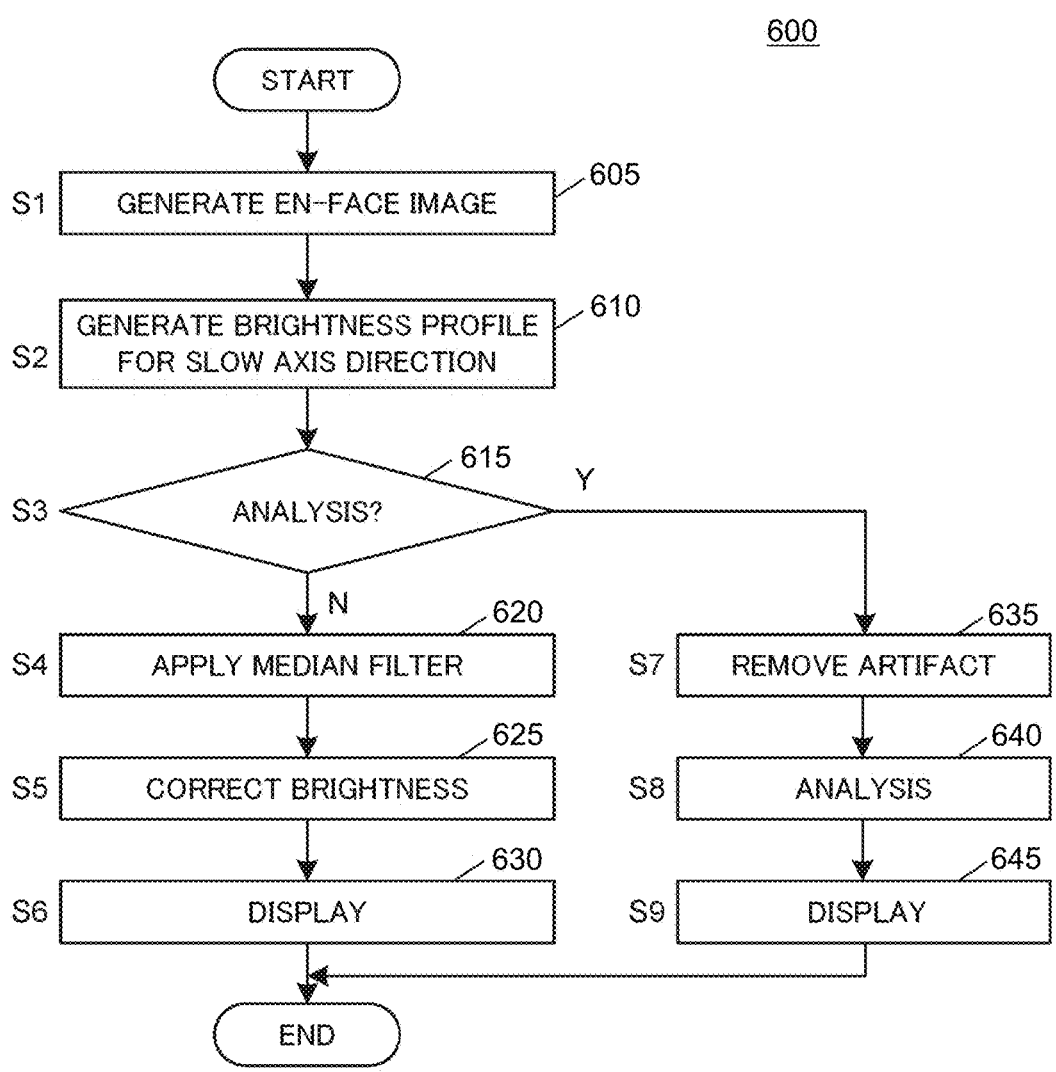
FIG. 6 is a schematic diagram illustrating an example of the operation of the ophthalmic image processing apparatus according to the embodiment.

FIG. 6 shows a flow chart 600 of an operation example of the ophthalmic image processing apparatus 1 according to the present embodiment. FIG. 6 shows an example of the flow of processes according to the display control program 22 and the data processing program 23.

(S1)

Based on the data input via the data input and output unit 30, the controller 10, for example, controls the data processor 40 (front image forming unit 412) to form, at step 605 (also referred to herein as "S1") an en-face image in which the blood vessel regions in the fundus of the subject's eye are enhanced. For example, as shown in FIG. 5A, an en-face image in which artifacts are depicted is formed. The controller 10 stores the image data of the formed en-face image in the storage unit 20.

(S2)

The controller 10 controls the first brightness profile generation unit 417A to generate, at step 610 (also referred to herein as "S2"), the first brightness profile along the Y direction by averaging the brightness values of the image data of the en-face image formed in the step S1 in the X direction. Here, the Y direction corresponds to the slow axis direction, and the X direction corresponds to the fast axis direction. For example, the first brightness profile PF1 shown in FIG. 4 is generated.

(S3)

The controller 10 determines, at step 615 (also referred to herein as "S3"), whether or not to execute predetermined analysis processing on the en-face image formed in the step S1. The analysis processing is executed according to a predetermined control sequence or executed when the user gives an instruction using the operation unit 50. The controller 10 determines whether or not to execute the analysis processing based on the predetermined control sequence or the content of the user's instruction input using the operation unit 50. When it is determined that the analysis processing is to be performed (S3: Y), the operation of the ophthalmic image processing apparatus 1 moves to step 635 (also referred to herein as "S7"). When it is determined that the analysis processing is not to be performed (S3: N), the operation of the ophthalmic image processing apparatus 1 moves to step 620 (also referred to herein as "S4").

(S4)

When it is determined that the analysis processing is not to be performed (S3: N), the controller 10 controls the second brightness profile generation unit 417B to generate a second brightness profile by applying a median filter, at step 620, having the median size of 9 to the first brightness profile generated in the step S2. For example, the second brightness profile PF2 shown in FIG. 4 is generated.

(S5)

The controller 10 controls the brightness correction unit 418 to perform the brightness correction, at step 625 (also referred to herein as "S5"), according to the formula (1) for each pixel using the first brightness profile obtained in the step S3 and the second brightness profile obtained in the step S4. The image data on which the brightness correction has been performed by the brightness correction unit 418 is stored in the storage unit 20.

(S6)

Based on the image data on which the brightness correction has been performed in the step S5, the display controller 11 displays, at step 630 (also referred to herein as "S6"), an image on the display device 2. Thereby, for example, an en-face image in which the artifacts have been removed or reduced as shown in FIG. 5B is displayed on the display device 2. This terminates the present operation of the ophthalmic image processing apparatus 1 (END).

(S7)

When it is determined in the step S3 that the analysis processing is to be performed (S3: Y), the controller 10 controls the specification unit 419 to specify the artifact regions, at step 635 (also referred to herein as "S7"), from the first brightness profile generated in the step S3.

(S8)

The controller 10 controls the analysis unit 42, at step 640 (also referred to herein as "S8"), to execute the removal of the artifact regions specified in the step S7 from the en-face image generated in S1 and the predetermined analysis processing on the en-face image from which the artifact regions have been removed.

(S9)

The display controller 11 displays, at step 645 (also referred to herein as "S9"), an image on the display device 2 based on the information obtained through the analysis processing in the step S8. For example, in the step S8, the analysis unit 42 removes the artifact regions and analyzes the resultant en-face image to obtain visualization information for visualizing the ischemic states of the fundus or the sites of the capillary vessels in the damaged sites. In this case, in the step S9, more accurate visualization information can be acquired without being affected by the artifacts. This terminates the present operation of the ophthalmic image processing apparatus 1 (END).

[Examples of Display Screen and Usage Mode]

For example, the ophthalmic image processing apparatus 1 can display the images in the step S6 or S9 on a part of the GUI screen described below.

A typical usage mode of the ophthalmic image processing apparatus 1 will be described below together with an example of the display screen. In the following example, the controller 10 displays a GUI screen or the like based on the GUI template 21 and the display control program 22, and displays an image or the like based on the display control program 22. In addition, the data processor 40 executes various processes based on the data processing program 23.

First, the user (doctor, etc.) of the ophthalmic image processing apparatus 1 inputs an instruction to start using the GUI. Upon receiving this instruction, the display controller 11 (GUI display controller 111) activates the display control program 22 and displays the GUI screen on the display device 2 based on the GUI template 21. The user inputs the patient ID to the GUI screen using the operation unit 50. Alternatively, the ophthalmic image processing apparatus 1 receives the patient ID by reading a patient card or the like with a card reader included in the data input and output unit 30. The method of entering the patient ID is not limited to these methods. In some cases, it is not necessary to input the patient ID as in the case where the three-dimensional data set D stored in the recording medium is input to the ophthalmic image processing apparatus 1.

By controlling the communication device included in the data input and output unit 30, the controller 10 sends the inputted patient ID to the image management server via the network. The image management server receives the patient ID, searches for the image data associated with the patient ID, and transmits the retrieved image data to the ophthalmic image processing apparatus 1. At this stage, for example, all or some pieces of image data acquired in the past for the concerned subject's eye (and the fellow eye of the concerned patient) are retrieved and transmitted. The image data transmitted from the image management server includes the three-dimensional data set D.

The communication device included in the data input and output unit 30 receives the image data transmitted from the image management server. The controller 10 stores the received image data together with the patient ID in the storage unit 20. With this, the image data including at least the three-dimensional data set D is stored in the storage unit 20. It should be noted that in the present example, the three-dimensional data set D is assumed to be image data representing a three-dimensional region of the fundus and that the three-dimensional region is represented in the image data of the fundus image (fundus photograph).

The GUI display controller 111 displays a list of image data of the concerned subject's eye (or of the concerned patient) on the GUI screen. The user selects desired image data using the operation unit 50. Here, it is assumed that the three-dimensional data set D is selected. The controller 10 reads out the selected three-dimensional data set D from the storage unit 20 and sends it to the data processor 40.

Figure 7:
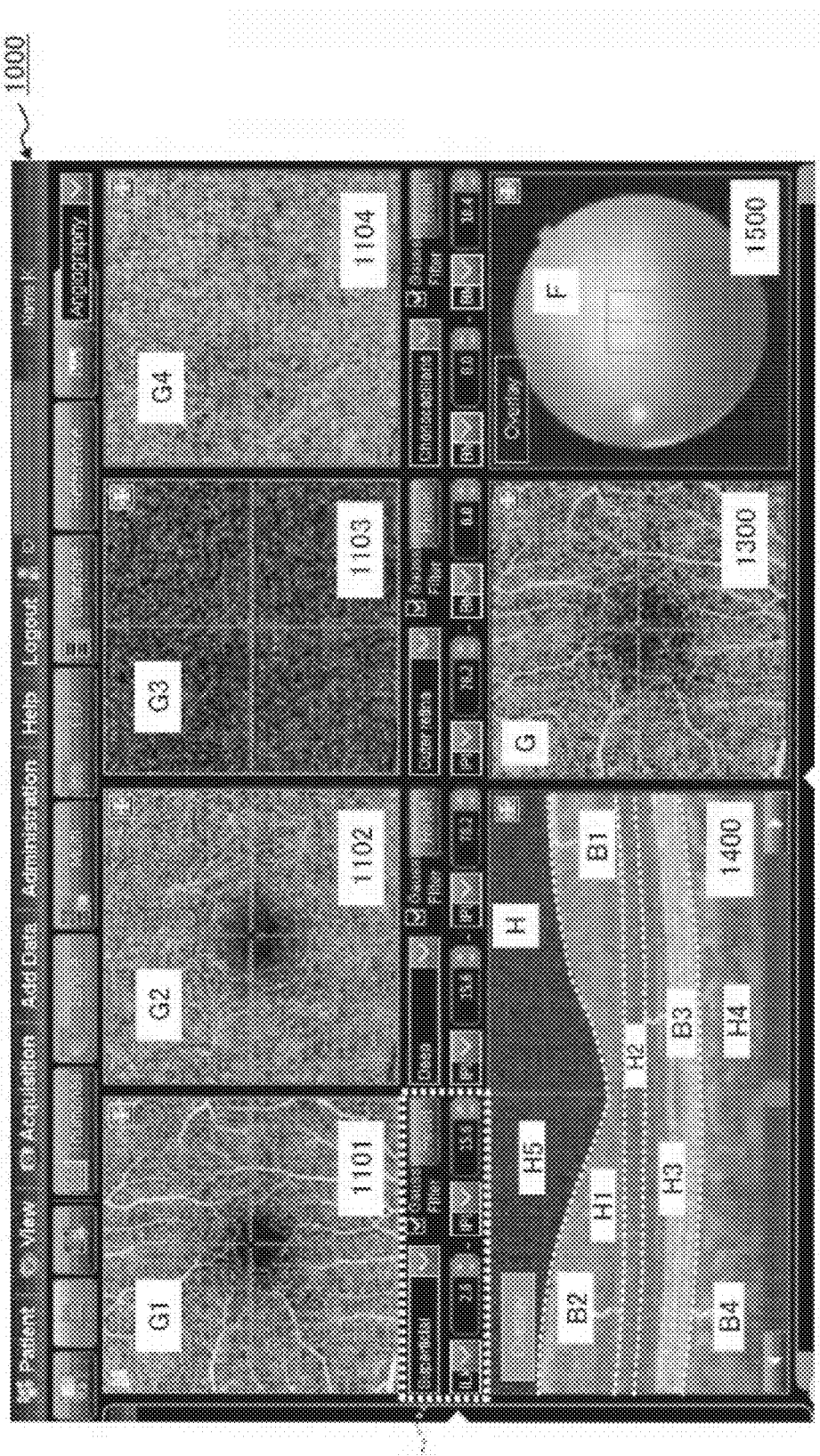
FIG. 7 is a schematic diagram illustrating an example of a screen displayed by the ophthalmic image processing apparatus according to the embodiment.

In the present example, the GUI screen 1000 shown in FIG. 7 is displayed on the display device 2 at this stage. On the GUI screen 1000, a plurality of image display regions is provided together with various software keys. More specifically, the plurality of image display regions includes four image display regions (the front image display regions 1101 to 1104) provided in the upper row and three image display regions (the B mode image display region 1400, the synthetic front image display region 1300, and the fundus image display region 1500) provided in the lower row.

In the front image display regions 1101 to 1104, front images constructed based on the three-dimensional data set D are displayed. In at least one of the front image display regions 1101 to 1104 (for example, in the front image display region 1101), an en-face image on which the brightness correction has been performed in the step S5 may be displayed. The frame portion of each of the front image display regions 1101 to 1104 is displayed in a predetermined color. The colors of the four frame portions are all different. For example, the frame portions of the front image display regions 1101 to 1104 are displayed in orange, yellowish green, sky blue, and blue, respectively.

Below each of the front image display regions 1101 to 1104, the condition setting unit 1200 for setting conditions related to front images is provided. The condition setting unit 1200 includes various software keys. The condition setting unit 1200 of the present example includes the following software keys: a pull-down menu for selecting a slice area to be imaged from among predetermined options (e.g., superficial, deep, outer retina, choriocapillaris, etc); a check box for selecting whether or not to apply a Gaussian filter; a pull-down menu for selecting a layer (or a boundary) of the fundus that is to be the upper edge of the slice area; an offset display section and an up-down button for moving the position of the upper edge in the depth direction (Z direction); a pull-down menu for selecting a layer (or a boundary) of the fundus that is to be the lower edge of the slice area; an offset display section and an up-down button for moving the position of the lower edge in the depth direction; and a reset button to reset the current setting contents. Typical examples of options for the upper edge and the lower edge of the slice area include ILM (inner limiting membrane), NFL/GCL (nerve fiber layer/ganglion cell layer boundary), IPL/INL (inner plexiform layer/inner nuclear layer boundary), IS/OS (inner segment/outer segment junction), RPE (retinal pigment epithelium), BM (Bruch membrane), CSI (choroid/sclera interface), and the like. The user can set a desired boundary (here, a tissue and a tissue boundary are collectively referred to as a boundary) in each of the upper edge pull-down menu and the lower edge pull-down menu, and furthermore, can set the offset of each of the upper edge and the lower edge by operating the up-down buttons with reference to the B mode image, etc. The region in the three-dimensional data set D corresponding to the set boundary is specified based on the result of segmentation of the three-dimensional data set D.

In the lower row, the B mode image display region 1400, the synthetic front image display region 1300, and the fundus image display region 1500 are arranged in order from the left side.

At this stage, the image of the subject's eye is not displayed on the GUI screen 1000. However, the fundus image may already be displayed in the fundus image display region 1500 at this stage.

The B mode image forming unit 415 of the data processor 40 forms a B mode image based on the three-dimensional data set D. The setting of the cross section for the formation of the B mode image is executed by the user or the B mode image forming unit 415. The B mode image display controller 114 displays the formed B mode image H in the B mode image display region 1400 (see FIG. 7). The user can perform operations for changing the B scan plane. For example, by moving the slider provided under the B mode image display area 1400 in the left-right direction, the B scan plane can be moved in the parallel direction. The B mode image forming unit 415 forms a new B mode image representing a cross section corresponding to the position of the slider. The B mode image display controller 114 updates the B mode image H with the new B mode image.

The segmentation processor 411 performs the segmentation of the three-dimensional data set D. In the present example, the segmentation is executed to specify a plurality of partial data sets corresponding to a plurality of layer tissues of the retina, a partial data set corresponding to the choroid, and a partial data set corresponding to the vitreous body. The B mode image display controller 114 can change the display modes of the image regions in the B mode image H corresponding to the layer tissues and/or the boundaries specified by the segmentation.

The user can refer to the B mode image H to set a desired slice area. When a slice area and the like are set using the condition setting unit 1200, the front image forming unit 412 forms a front image based on the set slice area. The front image display controller 112 displays the formed front image in the front image display region corresponding to the condition setting unit 1200 (e.g., in one of the front image display regions 1101 to 1104 arranged above the condition setting unit 1200). By repeating such operations and processing, the front images G1 to G4 are displayed in the front image display regions 1101 to 1104, respectively (see FIG. 7).

The color transformation unit 413 converts at least one front image of the four front images G1 to G4, which are gray scale images, into a (partial) color image. The color given to the front image is the same as that of the frame portion of the front image display region in which the front image is displayed. For example, the color transformation unit 413 performs one or more of the following four processes: assigning orange color, which is the same color as the frame portion of the front image display region 1101, to the pixels of the blood vessel regions depicted in the front image G1; assigning yellowish green color, which is the color as the frame portion of the front image display region 1102, to the pixels of the blood vessel regions depicted in the front image G2; assigning sky blue color, which is the same color as the frame portion of the front image display region 1103, to the pixels of the blood vessel regions depicted in the front image G3; and assigning blue color, which is the same color as the frame portion of the front image display region 1104, to the pixels of the blood vessel regions depicted in the front image G4.

The synthetic front image forming unit 414 forms a synthetic front image by synthesizing a plurality of front images including part of or all the front images converted into a (partial) color images by the color transformation unit 413. In addition, the synthetic front image forming unit 414 forms the synthetic front image G by synthesizing three front images G1 to G3 of the four front images G1 to G4. The synthetic front image display controller 113 displays the formed synthetic front image G in the synthetic front image display region 1300. The front images G1 to G3 are blood vessel enhanced images (angiograms) at different depth positions. Therefore, when the three front images G1 to G3 shown in FIG. 7 are synthesized, the formed synthetic front image G includes the blood vessel regions in the front image G1 expressed in orange color, the blood vessel regions in the front image G2 expressed in yellowish green color, and the blood vessel regions in the front image G3 expressed in sky blue color. In other words, the blood vessels present at various depths are expressed so as to be distinguishable by the colors corresponding to the depth positions.

The segment specification unit 416 specifies the partial regions of the B mode image H respectively corresponding to the slice areas (i.e., segments) of the front images G1 to G4. The segment display controller 115 displays the segment information indicating the partial region of the B mode image H specified by the segment specification unit 416 on the B mode image H. Each piece of segment information is displayed in the color assigned to the corresponding front image.

FIG. 7 shows a display example of the segment information. In the present example, the slice area of the front image G1 is set to "Superficial", the slice area of the front image G2 is set to "Deep", the slice area of the front image G3 is set to "Outer retina", and the slice area of the front image G4 is set to "Choriocapillaris".

The slice area of the front image G1 corresponds to the partial region H1 having the boundary B1 as the upper edge and the boundary B2 as the lower edge, and the partial region H1 is presented in orange color (the color of the frame portion 1101a) as the segment information representing it. The slice area of the front image G2 corresponds to the partial region H2 having the boundary B2 as the upper edge and the boundary B3 as the lower edge, and the partial region H2 is presented in yellowish green color (the color of the frame portion 1102a) as the segment information representing it. The slice area of the front image G3 corresponds to the partial region H3 having the boundary B3 as the upper edge and the boundary B4 as the lower edge, and the partial region H3 is presented in sky blue color (the color of the frame portion 1103a) as the segment information representing it. The slice area of the front image G4 corresponds to the partial region H4 having the boundary B4 as the upper edge, and the partial region H4 is presented in blue color (the color of the frame portion 1104a) as the segment information representing it. It should be noted that the reference symbol "H5" denotes the partial region corresponding to the vitreous body.

Here, it is not necessary to present the segment information for all of the front images G1 to G4. For example, the pieces of segment information can be presented only for the front images G1 to G3 used for forming the synthetic front image G.

The user can designate a desired front image from among the front images G1 to G4. The designation of a desired front image is performed by clicking one or more front images using a pointing device included in the operation unit 50, for example. The segment display controller 115 displays only the segment information corresponding to the designated front image. For example, when the front image G1 is designated, segment information is given only to the partial region H1 corresponding to the designated front image G1 (that is, it is displayed in orange color), and the other partial regions H2 to H5 are displayed in gray scale. As a result, it is possible to easily grasp the segment corresponding to the front image of interest. Note that a segment corresponding to the specified front image may be displayed in a pseudo color so that this segment can be observed in detail.

The user can select front images to be used for forming a synthetic front image. This selection is made, for example, by clicking two or more front images using a pointing device included in the operation unit 50. It is also possible to delete or replace any of the front images used to form the current synthetic front image, or to add a new front image. The synthetic front image forming unit 414 forms a new synthetic front image based on a new combination of front images (including the front image to which color transformation is performed). The synthetic front image display controller 113 displays the new synthetic front image instead of the current synthetic front image. As a result, it is possible to observe a synthetic front image according to a combination of front images designated by the user.

It is also possible to configure to automatically select a front image. For example, it is possible to select a front image based on the slice area having been set. As a specific example, when part of the choroid, part of the vitreous body, or the like is designated as a slice area, it is possible to exclude such a slice area from the subject of synthetic front image formation. Many of small blood vessels are distributed in the choroid and thus, when a color is assigned to the blood vessel regions, the whole front image seems to be lightly colored, which may hinder the grasp of the distribution of blood vessels of the retina. As for the vitreous body, it is generally unnecessary for observation of blood vessels of the fundus. On the other hand, when observing abnormality of the vitreous body such as vitreous traction, it is possible to form a synthetic front image including a slice area that includes part of the vitreous body. In addition, when it is desired to observe the contact surface between the vitreous body and the retina or the vitreous body in the vicinity of the retina, it is possible to form a synthetic front image including a slice area that includes part of the vitreous body. Further, it is possible to switch the slice area that is the subject of synthetic front image formation according to the type of the three-dimensional data set D (e.g., a blood vessel enhanced image, a morphological image, a blood flow dynamic image, etc.).

The user can arbitrarily change the slice area of a desired front image among the current front images G1 to G4. The condition setting unit 1200 is used to change the slice area. The user sets a desired slice area by operating a software key in the condition setting unit 1200 using a pointing device (a mouse, etc.) included in the operation unit 50.

For example, when the slice area of the front image G1 is changed, the front image forming unit 412 forms a new front image based on the newly set slice area. The front image display controller 112 displays the new front image instead of the current front image G1.

In addition, the color transformation unit 413 assigns the color (orange color) corresponding to the front image G1 to part of the new front image (blood vessel regions etc. in the new front image). The synthetic front image forming unit 414 uses the new front image instead of the front image G1 to form a new synthetic front image. The synthetic front image display controller 113 displays the new synthetic front image instead of the current synthetic front image G. In the new synthetic front image, the blood vessel regions etc. in the new front image is expressed in the same color as that of the front image G1 before updating.

Further, the segment specification unit 416 newly determines the partial region of the B mode image H corresponding to the slice area of the new front image. The segment display controller 115 displays new segment information indicating the newly specified partial region instead of the segment information corresponding to the current front image G1.

According to such a configuration, it is possible to automatically update the front image, update the synthetic front image, and update the segment information, in response to arbitrary change in the slice area of the front image.

On the GUI screen 1000, a software key or a check box (selection widget) may be displayed for selecting whether or not to perform brightness correction by the brightness correction unit 418. In this case, the designation as to whether or not to perform the brightness correction by the brightness correction unit 418 is performed by clicking the software key or the check box using a pointing device included in the operation unit 50, for example. When it is designated that the brightness correction is to be performed, the en-face image (s) on which the brightness correction has been performed in the step S5 (for example, the en-face image shown in FIG. 5B) is displayed in at least one of the front image display regions 1101 to 1104 (for example, in the front image display region 1101). When it is designated that the brightness correction is not to be performed, the en-face image(s) before the brightness correction formed by the front image forming unit 412 (for example, the en-face image shown in FIG. 5A) is displayed in at least one of the front image display regions 1101 to 1104 (for example, in the front image display region 1101). The designation of whether or not to perform the brightness correction by the brightness correction unit 418 may be received after displaying the en-face image on which the brightness correction has been performed and the en-face image on which the brightness correction has not been performed side by side.

In the embodiment described above, the brightness profile for the slow axis direction is generated for an en-face image in which the blood vessel regions are enhanced, and the brightness correction is performed on the en-face image based on the generated brightness profile. However, the brightness correction according to the present embodiment is not limited to this. For example, when the brightness profile in the slow axis direction is generated for a B mode image in which the blood vessel regions are enhanced and the brightness correction of the concerned B mode image is performed, the brightness of the blood vessel regions enhanced in the en-face image and the brightness of the blood vessel regions enhanced in the B mode image may be substantially different. If this is so, there is a possibility that the blood flow portions are not enhanced, or conversely the portions other than the blood flow portions are enhanced. Therefore, in the case of removing or reducing the artifacts in the B mode image in which the blood vessel regions are enhanced, the first brightness profile generation unit 417A generates, for example, a first brightness profile along the Y direction by integrating the brightness values of the image data representing the projection image generated from the three-dimensional data set D. The brightness correction unit 418 performs brightness correction on the B mode image using the generated first brightness profile as described above. As a result, when performing brightness correction according to the present embodiment, an image can be acquired in which the blood vessel regions are enhanced with almost the same brightness as the brightness of the blood vessel regions depicted in the en-face image.

In the embodiment described above, the case of generating the brightness profile for the slow axis direction of the en-face image has been described, but the operation of the ophthalmic image processing apparatus 1 according to the present embodiment is not limited thereto. For example, the first brightness profile generation unit 417A may generate a brightness profile along the slow axis direction for the volume data as the three-dimensional data set D. More specifically, the first brightness profile generation unit 417A generates a first brightness profile along the slow axis direction of the projection image generated from the volume data. The second brightness profile generation unit 417B generates a second brightness profile from the generated first brightness profile as in the embodiment described above. With this, it becomes sufficient to generate only one first brightness profile along the slow axis direction from the volume data. Therefore, it becomes unnecessary to generate a first brightness profile each time an en-face image corresponding to a different position in the depth direction is displayed.

In the embodiment described above, the case has been mainly described where the second brightness profile generation unit 417B applies a predetermined filter to the first brightness profile, but the present embodiment is not limited to this.

Figure 8:
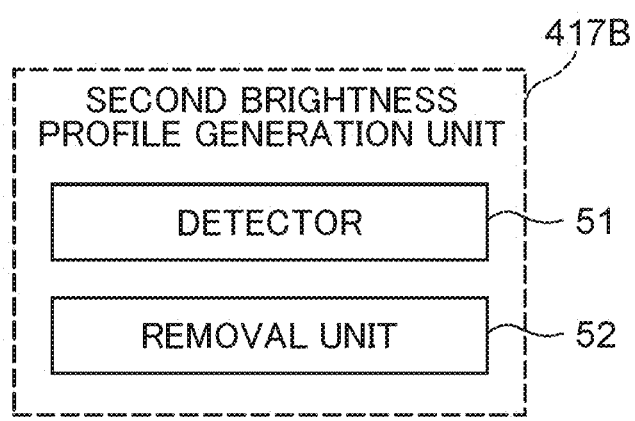
FIG. 8 is a schematic diagram illustrating an example of the configuration of the ophthalmic image processing apparatus according to a modification of the embodiment.

FIG. 8 shows a block diagram of a configuration example of the second brightness profile generation unit 417B according to a modification of the embodiment described above. The second brightness profile generation unit 417B shown in FIG. 8 includes the detector 51 and the removal unit 52. The detector 51 detects a peak of the first brightness profile. For example, the detector 51 detects a peak in the first brightness profile whose half width is equal to or less than a predetermined value and whose amplitude is equal to or larger than a predetermined level, and specifies the position of the peak detected. The removal unit 52 removes the peak detected by the detector 51. For example, the removal unit 52 removes the peak by changing the value of the brightness profile at the position of the peak specified by the detector 51 based on values of the brightness profile near the specified position. With this, the second brightness profile generation unit 417B can perform smoothing processing on the first brightness profile.

<Ophthalmic Imaging Apparatus>

Figure 9:
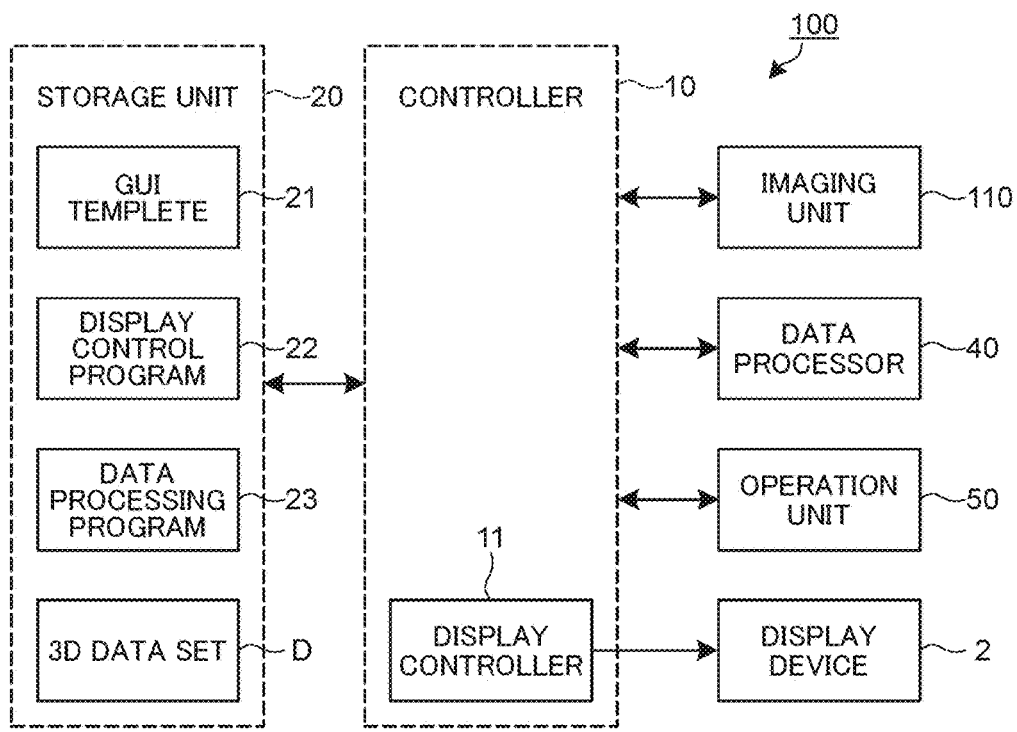
FIG. 9 is a schematic diagram illustrating an example of the configuration of the ophthalmic imaging apparatus according to the embodiment.

An ophthalmic imaging apparatus according to the present embodiment may include part of or all the components of the ophthalmic image processing apparatus of the embodiment described above. Exemplary configuration of the ophthalmic imaging apparatus is shown in FIG. 9. Components similar to those in the ophthalmic image processing apparatus 1 (FIG. 1) of the embodiment described above are denoted by the same reference symbols, and descriptions thereof will be omitted unless otherwise mentioned. The ophthalmic imaging apparatus 100 shown in FIG. 9 may include part of or all the components shown in FIG. 2. Further, the display screen and the displayed images may be the same as or similar to the aspects shown in FIG. 7. In addition, with regard to data processing such as image processing etc., it is possible to employ part of or all the processing described with reference to FIG. 6, and further, modifications thereof.

The ophthalmic imaging apparatus 100 has a function of acquiring data on the subject's eye using OCT and a function of displaying various information related to the subject's eye and a GUI for observing the image of the subject's eye on the display device 2. The display device 2 may be a part of the ophthalmic imaging apparatus 100 or may be an external device connected to the ophthalmic imaging apparatus 100.

The ophthalmic imaging apparatus 100 includes the controller 10, the storage unit 20, the data processor 40, the operation unit 50, and the imaging unit 110. The controller 10 includes the display controller 11. As in the embodiment described above, the storage unit 20 stores the GUI template 21, the display control program 22, the data processing program 23, and the three-dimensional data set D. The three-dimensional data set D is generated by the imaging unit 110 and stored in the storage unit 20. The controller 10, the storage unit 20, the data processor 40 and the operation unit 50 may include at least the same functions as those of the ophthalmic image processing apparatus 1 of the embodiment described above.

The imaging unit 110 two-dimensionally scans the fundus of the subject's eye in both the X direction and the Y direction using OCT to generate a three-dimensional data set (i.e., image data). The imaging unit 110 includes a configuration for performing measurement using, for example, spectral domain OCT or swept source OCT (e.g., an optical system, a drive system, a control system, etc.), and a configuration for forming image data based on the data acquired using OCT (e.g., a processor). For example, the image data forming processing includes processing such as Fast Fourier Transform (FFT) etc. as in the conventional OCT techniques, The imaging unit 110 scans a three-dimensional region of the subject's eye. The scanning mode at that time is, for example, a raster scan (or a three-dimensional scan). This raster scan is performed, for example, to scan each of a plurality of B cross sections a predetermined number of times, that is, to sequentially scan a plurality of B cross sections, each a predetermined number of times. The imaging unit 110 forms a plurality of cross sectional images (B mode images) for each B cross section based on the data acquired by the raster scan. By embedding these cross sectional images in a single three-dimensional coordinate system, stack data is formed. In the stack data, a predetermined number of cross sectional images corresponds to each B cross section. In addition, volume data (voxel data) is formed by applying interpolation processing or the like to the stack data. For the volume data as well, a predetermined number of voxel groups are assigned to the position corresponding to each B cross section. Stack data and volume data are examples of the three-dimensional data set D. The three-dimensional data set D constructed is stored in the storage unit 20 by the controller 10.

Based on the three-dimensional data set D thus obtained, the ophthalmic imaging apparatus 100 provides the same GUI, control and data processing as the ophthalmic image processing apparatus 1 of the embodiment described above. Based on the three-dimensional data set D, the data processor 40 forms a B mode image, a plurality of front images, and a synthetic front image in which part or all of these front images are synthesized. This process may be the same as the process performed by the image processor 41 of the embodiment described above (see FIG. 2).

The display controller 11 displays the B mode image, the plurality of front images and the synthetic front image formed by the data processor 40 in a predetermined layout on the display device 2. Further, the display controller 11 displays identification color information for identifying the plurality of front images by colors. Furthermore, the display controller 11 displays slice area information indicating the partial region of the B mode image corresponding to the slice area in the three-dimensional data set D represented by each of the plurality of front images, in a color corresponding to the identification color information. In addition, the display controller 11 displays a synthetic front image based on the plurality of front images, each expressed by a color corresponding to its identification color information.

In this way, it can be said that the ophthalmic imaging apparatus 100 includes the imaging unit (OCT function and OCT image forming function) in addition to the configuration of the ophthalmic image processing apparatus according to the embodiment described above. Further, the ophthalmic imaging apparatus 100 may include any items (configurations, controls, actions, effects, etc.) related to the ophthalmic image processing apparatus of the embodiment described above.

According to the ophthalmic imaging apparatus 100 thus configured, like the ophthalmic image processing apparatus 1 of the embodiment described above, it is possible to easily and comprehensively grasp the states of the eye at various depth positions.

[Actions/Effects]

The action and effects of the ophthalmic image processing apparatus and the ophthalmic imaging apparatus according to the above embodiments will be described.

The ophthalmic image processing apparatus (1) according to the above embodiment includes a storage unit (20), a first brightness profile generation unit (417A), a second brightness profile generation unit (417B), and a brightness correction unit (418). The storage unit is configured to store image data acquired through scanning a subject's eye using optical coherence tomography. The first brightness profile generation unit is configured to generate a first brightness profile (PF1) along a first direction (Y direction) by integrating brightness values of the image data. The second brightness profile generation unit is configured to processes the first brightness profile to generate a second brightness profile (PF2). The brightness correction unit is configured to perform brightness correction of the image data based on the first brightness profile and the second brightness profile.

According to such a configuration, the brightness correction of the image data is performed based on the first brightness profile along the first direction and the second brightness profile obtained by processing the first brightness profile. Therefore, it is possible to correct the brightness values affected by the artifacts in the first direction. This makes it possible to prevent the degradation in image quality based on the artifacts in the first direction depicted in the image acquired using OCT.

In addition, in the ophthalmic image processing apparatus according to the above embodiment, the brightness correction unit performs, for each of a plurality of positions in the first direction, the brightness correction on the pixel in the image data corresponding to a concerned position based on the value of the first brightness profile at the concerned position in the first direction and a value of the second brightness profile at the concerned position in the first direction.

According to such a configuration, since the brightness correction is performed for each pixel based on the value of the first brightness profile and the value of the second brightness profile, artifacts can be removed or reduced on a pixel-by-pixel basis.

In the ophthalmic image processing apparatus according to the above embodiment, the brightness correction unit may perform the brightness correction based on the ratio or the difference between the value of the first brightness profile and the value of the second brightness profile.

According to such a configuration, since the brightness correction is performed based on the ratio or the difference between the value of the first brightness profile and the value of the second brightness profile, it is possible to prevent the degradation in image quality based on the artifacts with a simple process.

Also, in the ophthalmic image processing apparatus according to the above embodiment, the second brightness profile generation unit may apply smoothing to the first brightness profile to generate the second brightness profile.

According to such a configuration, since the second brightness profile is generated by smoothing the first brightness profile, brightness correction can be performed to remove a jutting value (or a protrusion value), a value greatly apart from others (or a divergence value), or the like in the first brightness profile to remove or reduce artifacts.

Further, in the ophthalmic image processing apparatus according to the above embodiment, the second brightness profile generation unit may apply at least one of a median filter and a rolling ball filter to the first brightness profile.

According to such a configuration, it is possible to remove or reduce artifacts with a simple process by using a known median filter or a known rolling ball filter.

Furthermore, in the ophthalmic image processing apparatus according to the above embodiment, the second brightness profile generation unit may include a detector (51) configured to detect a peak of the first brightness profile and a removal unit (52) configured to remove the peak detected by the detector.

According to such a configuration, since the peak of the first brightness profile is detected and the detected peak is removed to remove the jutting value, a value greatly apart from others in the first brightness profile, the artifacts can be removed or reduced with a simpler process.

In the ophthalmic image processing apparatus according to the above embodiment, the second brightness profile generation unit may process only part of the first brightness profile.

According to such a configuration, since the second brightness profile is generated by local processing on the first brightness profile, artifacts can be removed or reduced with a minimum processing load.

An ophthalmic image processing apparatus (1) according to the above embodiment includes a storage unit (20), a first brightness profile generation unit (417A), a specification unit (419), and an analysis unit (42). The storage unit is configured to store image data acquired through scanning a subject's eye using optical coherence tomography. The first brightness profile generation unit is configured to generate a first brightness profile along a first direction (Y direction) by integrating brightness values of the image data. The specification unit is configured to specify a partial region of the image data based on the first brightness profile. The analysis unit is configured to remove the partial region specified by the specification unit and analyze the image data from which the partial region has been removed.

According to such a configuration, a partial region of the image data is specified based on the first brightness profile along the first direction, and the image data is analyzed after the partial region specified is removed. Therefore, it is possible to analyze the image data without being affected by the artifacts in the first direction. This makes it possible to prevent the decrease in reliability of the analysis result based on the artifacts in the first direction depicted in the image acquired using OCT.

In the ophthalmic image processing apparatus according to the above embodiment, the image data is three-dimensional image data formed by arranging a plurality of B mode images in the first direction, wherein each of the plurality of B mode images lies along a second direction (X direction) orthogonal to the first direction, or the image data is front image data generated based on the three-dimensional image data. In addition, the first brightness profile generation unit may integrate the brightness values in the second direction.

According to such a configuration, the first brightness profile is generated: by integrating the brightness values, in the second direction, of the three-dimensional image data formed by arranging a plurality of B mode images in the first direction, wherein each of the plurality of B mode images lies along the second direction; or by integrating the brightness values of the front image data generated based on the three-dimensional image data in the second direction. Therefore, it is possible to correct the brightness values affected by the artifacts in the first direction. This makes it possible to prevent the degradation in image quality or the decrease in reliability of the analysis result based on the artifacts in the first direction depicted in the image acquired using OCT.

An ophthalmic imaging apparatus (100) according to the above embodiment includes an imaging unit (110), a first brightness profile generation unit (417A), a second brightness profile generation unit (417B), and a brightness correction unit (418). The imaging unit is configured to scan a subject's eye using optical coherence tomography to generate image data. The first brightness profile generation unit is configured to generate a first brightness profile (PF1) along a first direction by integrating brightness values of the image data. The second brightness profile generation unit is configured to process the first brightness profile to generate a second brightness profile (PF2). The brightness correction unit is configured to perform brightness correction of the image data based on the first brightness profile and the second brightness profile.

According to such a configuration, the brightness correction of the concerned image data is performed based on the first brightness profile along the first direction and the second brightness profile obtained by processing the first brightness profile. Therefore, it is possible to provide an ophthalmic imaging apparatus capable of correcting the brightness values affected by the artifacts in the first direction. This makes it possible to prevent the degradation in image quality based on the artifacts in the first direction depicted in the image acquired using OCT.

An ophthalmic imaging apparatus (100) according to the above embodiment includes an imaging unit (110), a first brightness profile generation unit (417A), a specification unit (419), and an analysis unit (42). The imaging unit is configured to scan a subject's eye using optical coherence tomography to generate image data. The first brightness profile generation unit is configured to generate a first brightness profile along a first direction (Y direction) by integrating brightness values of the image data. The specification unit is configured to specify a partial region of the image data based on the first brightness profile. The analysis unit is configured to remove the partial region specified by the specification unit and analyze the image data from which the partial region has been removed.

According to such a configuration, a partial region of the image data is specified based on the first brightness profile along the first direction, and the specified partial region is removed to analyze the concerned image data. Therefore, it is possible to provide an ophthalmic imaging apparatus capable of analyzing image data without being affected by the artifacts in the first direction. This makes it possible to prevent the decrease in reliability of the analysis result based on the artifacts in the first direction depicted in the image acquired using OCT.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic image processing apparatus comprising:
   a storage unit configured to store image data acquired through scanning a subject's eye using optical coherence tomography;
   a first brightness profile generation unit configured to generate a first brightness profile along a first direction by integrating brightness values of the image data;
   a second brightness profile generation unit configured to process the first brightness profile to generate a second brightness profile; and
   a brightness correction unit configured to perform brightness correction of the image data based on the first brightness profile and the second brightness profile,
   wherein the image data is front image data generated based on three-dimensional image data formed by arranging a plurality of B mode images in the first direction, each of the plurality of B mode images lying along a second direction orthogonal to the first direction, and
   wherein the front image data corresponds to slice areas of the plurality of B mode images.

2. The ophthalmic image processing apparatus of claim 1, wherein the brightness correction unit performs, for each of a plurality of positions in the first direction, the brightness correction on a pixel in the image data corresponding to a concerned position based on a value of the first brightness profile at the concerned position in the first direction and a value of the second brightness profile at the concerned position in the first direction.

3. The ophthalmic image processing apparatus of claim 2, wherein the brightness correction unit performs the brightness correction based on a ratio or a difference between the value of the first brightness profile and the value of the second brightness profile.

4. The ophthalmic image processing apparatus of claim 1, wherein the second brightness profile generation unit applies smoothing to the first brightness profile to generate the second brightness profile.

5. The ophthalmic image processing apparatus of claim 4, wherein the second brightness profile generation unit applies at least one of a median filter and a rolling ball filter to the first brightness profile.

6. The ophthalmic image processing apparatus of claim 4, wherein the second brightness profile generation unit comprises:
   a detector configured to detect a peak of the first brightness profile; and
   a removal unit configured to remove the peak detected by the detector.

7. The ophthalmic image processing apparatus of claim 1, wherein the second brightness profile generation unit processes only part of the first brightness profile.

8. An ophthalmic imaging apparatus comprising:
   an imaging unit configured to scan a subject's eye using optical coherence tomography to generate image data;
   a first brightness profile generation unit configured to generate a first brightness profile along a first direction by integrating brightness values of the image data;

a second brightness profile generation unit configured to process the first brightness profile to generate a second brightness profile; and a brightness correction unit configured to perform brightness correction of the image data based on the first brightness profile and the second brightness profile, wherein the image data is three-dimensional image data formed by arranging a plurality of B mode images in the first direction, wherein each of the plurality of B mode images lies along a second direction orthogonal to the first direction, and wherein the first brightness profile generation unit executes integration of the brightness values in the second direction.

9. The ophthalmic image processing apparatus of claim 1, wherein the front image data is en-face image data representing a transverse cross section.

10. An ophthalmic image processing apparatus comprising:

a storage unit configured to store image data acquired through scanning a subject's eye using optical coherence tomography;

a first brightness profile generation unit configured to generate a first brightness profile along a first direction by integrating brightness values of the image data;

a second brightness profile generation unit configured to process the first brightness profile to generate a second brightness profile; and a brightness correction unit configured to perform brightness correction of the image data based on the first brightness profile and the second brightness profile, wherein the image data is three-dimensional image data formed by arranging a plurality of B mode images in the first direction, wherein each of the plurality of B mode images lies along a second direction orthogonal to the first direction, and wherein the first brightness profile generation unit executes integration of the brightness values in the second direction.

\* \* \* \* \*